US008673946B2

United States Patent
Andjelkovic et al.

(10) Patent No.: US 8,673,946 B2
(45) Date of Patent: *Mar. 18, 2014

(54) 4-TRIMETHYLAMMONIO-BUTYRATES AS CPT2 INHIBITORS

(71) Applicant: Hoffmann-La Roche Inc., Nutley, NJ (US)

(72) Inventors: Mirjana Andjelkovic, Basel (CH);
Simona M. Ceccarelli, Basel (CH);
Odile Chomienne, Altkirch (FR);
Patrizio Mattei, Riehen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/645,642

(22) Filed: Oct. 5, 2012

(65) Prior Publication Data

US 2013/0030033 A1   Jan. 31, 2013

Related U.S. Application Data

(63) Continuation of application No. 12/430,941, filed on Apr. 28, 2009, now Pat. No. 8,349,893.

(30) Foreign Application Priority Data

Apr. 29, 2008   (EP) ..................... 08155318

(51) Int. Cl.
| | | |
|---|---|---|
| A61K 31/205 | (2006.01) | |
| A61K 31/381 | (2006.01) | |
| C07D 333/24 | (2006.01) | |
| C07C 233/51 | (2006.01) | |
| C07C 231/12 | (2006.01) | |
| C07C 235/12 | (2006.01) | |
| A61P 13/12 | (2006.01) | |
| A61P 3/04 | (2006.01) | |
| A61P 9/12 | (2006.01) | |
| A61P 3/06 | (2006.01) | |
| A61P 9/04 | (2006.01) | |
| A61P 9/10 | (2006.01) | |
| A61P 3/00 | (2006.01) | |
| A61P 3/10 | (2006.01) | |
| C07D 333/20 | (2006.01) | |

(52) U.S. Cl.
CPC ............ *A61K 31/205* (2013.01); *A61K 31/381* (2013.01); *C07D 333/20* (2013.01); *C07D 333/24* (2013.01); *C07C 233/51* (2013.01); *C07C 231/12* (2013.01); *C07C 235/12* (2013.01)
USPC ........... 514/357; 514/365; 514/438; 546/335; 548/204; 548/205; 549/76

(58) Field of Classification Search
CPC .. C07D 213/40; C07D 277/24; C07D 333/20; C07D 333/24; A61K 31/205; A61K 31/381; C07C 233/51; C07C 231/12; C07C 235/12
USPC ........... 514/357, 365, 438; 546/335; 548/204, 548/205; 549/76
See application file for complete search history.

(56) References Cited

U.S. PATENT DOCUMENTS

| | | | |
|---|---|---|---|
| 4,632,925 A | 12/1986 | Mullin, Jr. et al. | |
| 6,444,701 B1 | 9/2002 | Giannessi et al. | |
| 8,344,027 B2 * | 1/2013 | Andjelkovic et al. | 514/563 |
| 8,349,893 B2 * | 1/2013 | Andjelkovic et al. | 514/554 |
| 2010/0105900 A1 | 4/2010 | Pauls et al. | |

FOREIGN PATENT DOCUMENTS

| | | |
|---|---|---|
| EP | 127098 | 12/1984 |
| WO | 99/59957 | 11/1999 |
| WO | 2006/092204 | 9/2006 |
| WO | 2008/015081 | 2/2008 |
| WO | 2008/109991 | 9/2008 |

OTHER PUBLICATIONS

Copending U.S. Appl. No. 13/556,250, filed Jul. 24, 2012.*
Silverman, The Organic Chemistry of Drug Design and Drug Action:15-20 ( 1992).
Jackson et al., Biochem. J. 341:483-489 ( 1999).
Giannessi et al., J. Med. Chem. (Database CA Online Chemical Abstracts Service, XP002539907, database accession No. 2002:954524), 46(2):303-309 ( 2003).
Intl Search Report for PCT/EP2009/054637 dated Sep. 3, 2009.
Jackson et al., J. Biol. Chem. 275:19560-19566 ( 2000).
Lin et al., J. Org. Chem. 72:9471-9480 ( 2007).
Evans et al., Tetrahedron 59:7973-7981 ( 2003).

* cited by examiner

*Primary Examiner* — Rosalynd Keys

(57) ABSTRACT

This invention relates to novel 4-trimethylammoniobutyrates of the formula $$\text{H}_3\text{C}-\overset{+}{\text{N}}(\text{CH}_3)_2-\text{CH}_2-\text{CH}(\text{HN-CO-(CH}_2)_m-\text{A}^1-(\text{CH}_2)_n-\text{R}^1)-\text{CH}_2-\text{COO}^- \quad I$$

wherein $A^1$, $R^1$, m and n are as defined in the description and in the claims, as well as pharmaceutically acceptable salts thereof. These compounds inhibit carnitine palmitoyl transferase (CPT) activity, in particular CPT2 activity, and can be used as medicaments.

16 Claims, No Drawings

4-TRIMETHYLAMMONIO-BUTYRATES AS CPT2 INHIBITORS

PRIORITY TO RELATED APPLICATION(S)

This application is a continuation application of U.S. Ser. No. 12/430,941, filed Apr. 28, 2009, and claims the benefit of European Patent Application No. 08155318.2, filed Apr. 29, 2008, which are hereby incorporated by reference in their entirety.

FIELD OF THE INVENTION

This invention is concerned with novel 4-trimethylammoniobutyrates as CPT2 inhibitors, a process for the manufacture of these compounds, pharmaceutical preparations which contain such compounds as well as the use of these compounds for the production of medicaments.

SUMMARY OF THE INVENTION

More specifically, the invention relates to compounds of the formula $$\text{Structure I}$$

wherein
$A^1$ is O or a bond,
m is selected from 3, 4, 5, 6, 7, 8, 9 and 10,
n is selected from 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

DETAILED DESCRIPTION

More specifically, the invention relates to compounds of the formula $$\text{Structure I}$$

wherein
$A^1$ is O or a bond,
m is selected from 3, 4, 5, 6, 7, 8, 9 and 10,
n is selected from 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

Elevated plasma levels of free fatty acids (FFAs) cause acute and long-term peripheral and hepatic insulin resistance. Increased plasma FFA levels and increase FFA oxidation are associated with type 2 diabetes. Hyperglycemia after an overnight fast is a major hallmark and an important diagnostic criterion of diabetes, and excessive gluconeogenesis is mainly responsible for the postabsorptive hyperglycemia in diabetic patients. High levels of free fatty acids (FFA) lead to an increase of liver mitochondrial β-oxidation, which results in increased concentrations of acetyl CoA. This provides increased energy (ATP) and reducing force (NADH) for gluconeogenesis. Increased acetyl CoA levels also stimulate gluconeogenesis by an allosteric activation of pyruvate carboxylase. Thereby, reduction of excessive liver β-oxidation, which is crucial to drive efficient gluconeogenesis, should lead to a reduction of fasting hyperglycemia in diabetic patients. The mitochondrial oxidation of long-chain FFA requires the intervention of two membrane-bound carnitine-dependent palmitoyltransferases (CPTs). CPT1, the outer mitochondrial membrane enzyme, catalyzes the formation of long-chain acylcarnitines. Liver (L-CPT1) and muscle (M-CPT1) CPT1 isoforms are encoded by two different genes and inhibited by malonyl-CoA. The N-terminal domain of L-CPT1 confers its lower sensitivity to malonyl CoA. CPT2, the inner mitochondrial membrane enzyme, reconverts long-chain acylcarnitines into long-chain acyl CoA esters. Long-chain acyl-CoAs are then β-oxidized to acetyl-CoA, which activates the pyruvate carboxylase and gluconeogenesis. According to the mechanism of action described above, pharmaceutically active substances which inhibit transport of long chain FFA though the inhibition of CPTs, reduce liver β-oxidation, consequently inhibit gluconeogenesis and therefore counteract hyperglycemia.

The present invention relates to novel compounds which inhibit carnitine palmitoyl transferase (CPT) activity, in particular/preferentially CPT2 activity. The compounds of the present invention can be used as pharmaceutically active agents, which are useful in the prevention and/or treatment of diseases which are modulated by CPT inhibitors, in particular/preferentially CPT2 inhibitors, particularly diseases which are related to hyperglycemia and/or glucose tolerance disorders. Such diseases include e.g. diabetes and associated pathologies, non insulin dependent diabetes mellitus (also referred to as diabetes type II), obesity, hypertension, insulin resistance syndrome, metabolic syndrome, hyperlipidemia, hypercholesterolemia, fatty liver disease, atherosclerosis, congestive heart failure and renal failure.

The novel compounds of the present invention exceed the compounds known in the art, inasmuch as they inhibit in particular or preferentially CPT2 activity. They are therefore expected to have an enhanced therapeutic potential compared to the compounds already known in the art.

A. Definitions

Unless otherwise indicated, the following definitions are set forth to illustrate and define the meaning and scope of the various terms used to describe the invention herein.

In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. The term "$C_{1-10}$-alkyl" refers to a branched or straight-chain monovalent saturated aliphatic hydrocarbon radical of one to ten carbon atoms, such as e.g. methyl, ethyl, n-propyl, isopropyl, n-butyl, s-butyl, t-butyl, pentyl, 1,1,3,3-tetramethyl-butyl and the like. Lower alkyl groups as described below also are preferred alkyl groups.

The term "lower alkyl" or "$C_1$-$C_7$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

The term "lower halogenalkyl" or "halogen-$C_1$-$C_7$-alkyl" refers to lower alkyl groups as defined above wherein at least one of the hydrogen atoms of the lower alkyl group is replaced by a halogen atom, preferably fluoro or chloro, most preferably fluoro. Among the preferred lower halogenalkyl groups are trifluoromethyl, difluoromethyl, trifluoroethyl, 2,2-difluoroethyl, fluoromethyl and chloromethyl, with trifluoromethyl being especially preferred.

The term "alkoxy" or "lower alkoxy" refers to the group R'—O—, wherein R' is lower alkyl and the term "lower alkyl" has the previously given significance. Examples of lower alkoxy groups are e.g. methoxy, ethoxy, n-propoxy, isopropoxy, n-butoxy, isobutoxy, sec-butoxy and tert-butoxy, preferably methoxy and ethoxy and most preferred methoxy.

Compounds of formula (I) can form pharmaceutically acceptable salts. Compounds of formula (I) can form salts with bases. Examples of such salts are alkaline, earth-alkaline and ammonium salts such as e.g. Na-, K-, Ca- and trimethylammoniumsalt. Compounds of formula I can also form pharmaceutically acceptable acid addition salts. Examples of such pharmaceutically acceptable salts are salts of compounds of formula (I) with physiologically compatible mineral acids, such as hydrochloric acid, sulphuric acid or phosphoric acid; or with organic acids, such as methanesulphonic acid, p-toluenesulphonic acid, acetic acid, lactic acid, citric acid, fumaric acid, maleic acid, tartaric acid, succinic acid or salicylic acid. The term "pharmaceutically acceptable salts" refers to all these salts.

B. Detailed Description

In detail, the present invention relates to compounds of the formula

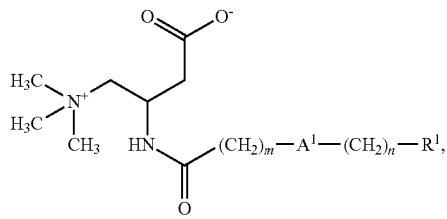

wherein
$A^1$ is O or a bond,
m is selected from 3, 4, 5, 6, 7, 8, 9 and 10,
n is selected from 1, 2, 3, 4 and 5,
$R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl, or heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl,
and pharmaceutically acceptable salts thereof.

Compounds of formula I are individually preferred and pharmaceutically acceptable salts thereof are individually preferred, with the compounds of formula I being particularly preferred.

Preferred are further compounds of formula I according to the invention, wherein $A^1$ is O (oxygen).

Preferred are further compounds of formula I according to the present invention, wherein m is selected from 6, 7, 8, 9 and 10. Especially preferred are compounds of formula I, wherein m is 7.

Further preferred are compounds of formula I according to the invention, wherein n is selected from 1, 2, 3 and 4, with those compounds being more preferred, wherein n is 1 or 2 and those compounds being especially preferred, wherein n is 1.

Especially preferred are compounds of formula I, wherein the sum of m and n is selected from 8, 9, 10 and 11.

A group of preferred compounds of formula (I) according to the invention are further those, wherein $R^1$ is aryl selected from phenyl and naphthyl, said aryl being unsubstituted or substituted by one, two, three, four or five groups selected from the group consisting of lower alkyl, halogen, lower halogenalkyl, lower alkoxy and phenyl.

Especially preferred are compounds of formula I according to the invention, wherein $R^1$ is phenyl substituted by one, two, three, four or five groups selected from the group consisting of lower alkyl, halogen, lower halogenalkyl, lower alkoxy and phenyl. More preferred are those compounds of formula I, wherein $R^1$ is phenyl substituted by one, two, three, four or five groups selected from the group consisting of lower alkyl, halogen, lower halogenalkyl, lower alkoxy and phenyl provided that at least one of the substituents is halogen or lower halogenalkyl. Especially preferred $R^1$ is phenyl substituted by one, two, three, four or five groups selected from halogen and lower halogenalkyl.

Another group of preferred compounds of formula I according to the present invention are those, wherein $R^1$ is heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl.

Especially preferred are compounds of formula I of the invention, wherein R¹ is thienyl. Furthermore, compounds of formula I having (R)-configuration are especially preferred, i.e. these are the compounds having the formula

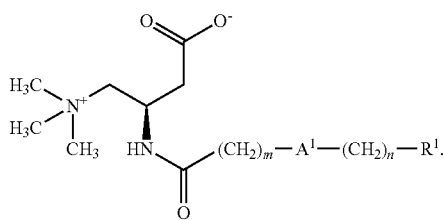

I-A

Preferred compounds of formula I are those selected from the group consisting of:
(R)-3-[8-(3,4-difluoro-benzyloxy)-octanoylamino]-4-trimethylammonio-butyrate,
(R)-3-[8-(2,5-difluoro-benzyloxy)-octanoylamino]-4-trimethylammonio-butyrate
(R)-3-[8-(2,4-difluoro-benzyloxy)-octanoylamino]-4-trimethylammonio-butyrate,
(R)-3-[8-(2,3,4-trifluoro-benzyloxy)-octanoylamino]-4-trimethylammonio-butyrate,
(R)-3-[8-(pentafluorophenylmethoxy)-octanoylamino]-4-trimethylammonio-butyrate,
(R)-3-[8-(4-trifluoromethyl-benzyloxy)-octanoylamino]-4-trimethylammonio-butyrate,
(R)-3-[8-(3-fluoro-4-trifluoromethyl-benzyloxy)-octanoylamino]-4-trimethylammonio-butyrate,
(R)-3-[8-(4-methoxy-benzyloxy)-octanoylamino]-4-trimethylammonio-butyrate,
(R)-3-[8-(biphenyl-4-ylmethoxy)-octanoylamino]-4-trimethylammonio-butyrate,
(R)-3-[8-(2-fluoro-4-trifluoromethyl-benzyloxy)-octanoylamino]-4-trimethylammonio-butyrate,
(R)-3-[8-(2,3,5,6-tetrafluoro-4-methoxy-benzyloxy)-octanoylamino]-4-trimethylammonio-butyrate,
(R)-3-[8-(naphthalen-1-ylmethoxy)-octanoylamino]-4-trimethylammonio-butyrate,
(R)-3-(8-benzyloxy-octanoylamino)-4-trimethylammonio-butyrate,
(R)—3-[8-(2-fluoro-benzyloxy)-octanoylamino]-4-trimethylammonio-butyrate,
(R)-3-[8-(3-fluoro-benzyloxy)-octanoylamino]-4-trimethylammonio-butyrate,
(R)-3-[8-(4-fluoro-benzyloxy)-octanoylamino]-4-trimethylammonio-butyrate,
(R)-3-[8-(2,3-difluoro-benzyloxy)-octanoylamino]-4-trimethylammonio-butyrate,
(R)-3-(10-phenyl-decanoylamino)-4-trimethylammonio-butyrate,
(S)-3-(10-phenyl-decanoylamino)-4-trimethylammonio-butyrate,
(R)-3-[10-(2-fluoro-phenyl)-decanoylamino]-4-trimethylammonio-butyrate,
(R)-3-[10-(2,5-dimethyl-phenyl)-decanoylamino]-4-trimethylammonio-butyrate,
(R)-3-[10-(2,6-dimethyl-phenyl)-decanoylamino]-4-trimethylammonio-butyrate,
(R)-3-[10-(4-methoxy-phenyl)-decanoylamino]-4-trimethylammonio-butyrate,
(R)-3-(10-naphthalen-1-yl-decanoylamino)-4-trimethylammonio-butyrate,
(R)-4-trimethylammonio-3-[10-(4-trifluoromethyl-phenyl)-decanoylamino]-butyrate,
(R)-3-[10-(3-fluoro-phenyl)-decanoylamino]-4-trimethylammonio-butyrate,
(R)-3-[10-(2,3-difluoro-phenyl)-decanoylamino]-4-trimethylammonio-butyrate,
(R)-3-(10-thiophen-3-yl-decanoylamino)-4-trimethylammonio-butyrate,
(R)-3-(6-phenyl-hexanoylamino)-4-trimethylammonio-butyrate,
(R)-3-(7-phenyl-heptanoylamino)-4-trimethylammonio-butyrate,
(R)-3-(8-phenyl-octanoylamino)-4-trimethylammonio-butyrate,
(R)-3-(9-phenyl-nonanoylamino)-4-trimethylammonio-butyrate,
(R)-3-(11-phenyl-undecanoylamino)-4-trimethylammonio-butyrate,
(R)-3-(12-phenyl-dodecanoylamino)-4-trimethylammonio-butyrate,
and pharmaceutically acceptable salts thereof.

Particularly preferred compounds of formula I are those selected from the group consisting of
(R)-3-[8-(4-trifluoromethyl-benzyloxy)-octanoylamino]-4-trimethylammonio-butyrate,
(R)-3-[8-(3-fluoro-4-trifluoromethyl-benzyloxy)-octanoylamino]-4-trimethylammonio-butyrate,
(R)-3-[8-(biphenyl-4-ylmethoxy)-octanoylamino]-4-trimethylammonio-butyrate,
(R)-3-[8-(naphthalen-1-ylmethoxy)-octanoylamino]-4-trimethylammonio-butyrate,
(R)-3-[8-(3-fluoro-benzyloxy)-octanoylamino]-4-trimethylammonio-butyrate,
(R)-3-(10-phenyl-decanoylamino)-4-trimethylammonio-butyrate,
(S)-3-(10-phenyl-decanoylamino)-4-trimethylammonio-butyrate,
(R)-3-[10-(2-fluoro-phenyl)-decanoylamino]-4-trimethylammonio-butyrate,
(R)-3-[10-(2,5-dimethyl-phenyl)-decanoylamino]-4-trimethylammonio-butyrate,
(R)-3-[10-(2,6-dimethyl-phenyl)-decanoylamino]-4-trimethylammonio-butyrate,
(R)-3-[10-(4-methoxy-phenyl)-decanoylamino]-4-trimethylammonio-butyrate,
(R)-3-(10-naphthalen-1-yl-decanoylamino)-4-trimethylammonio-butyrate,
(R)-3-[10-(3-fluoro-phenyl)-decanoylamino]-4-trimethylammonio-butyrate,
(R)-3-[10-(2,3-difluoro-phenyl)-decanoylamino]-4-trimethylammonio-butyrate,
(R)-3-(10-thiophen-3-yl-decanoylamino)-4-trimethylammonio-butyrate,
(R)-3-(12-phenyl-dodecanoylamino)-4-trimethylammonio-butyrate,
and pharmaceutically acceptable salts thereof.

It will be appreciated that the compounds of general formula I in this invention may be derivatised at functional groups to provide derivatives which are capable of conversion back to the parent compound in vivo.

The invention also relates to a process for the preparation of compounds of formula I as defined above, which process comprises
reacting a tertiary amine of formula

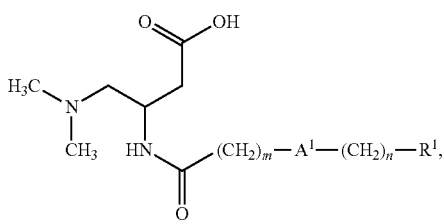

wherein $A^1$, m, n and $R^1$ are as defined hereinbefore,
with a methylating agent in the presence of a base in a polar solvent to obtain a compound of formula

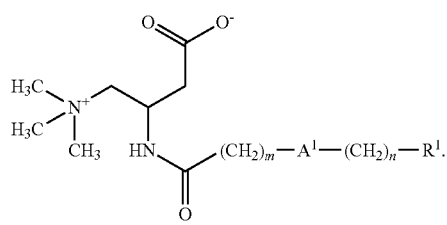

The methylating agent is preferably selected from iodomethane or trifluoromethanesulfonic acid methyl ester. "In the presence of a base" means preferably in the presence of sodium hydrogencarbonate or potassium hydrogencarbonate. The polar solvent is preferably selected from methanol or acetonitrile. Preferably, the reaction is carried out at temperatures between 0° C. and 60° C.

As compounds of formula I having (R)-configuration are preferred, tertiary amines of the formula

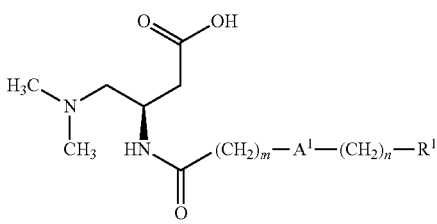

are preferably used in the process of the present invention.

The present invention also relates to compounds of formula I as defined above, when prepared by a process as described above.

In more detail, compounds of formula I of the present invention are synthesized from the corresponding tertiary amines II. The conversion of II to I is accomplished by using a methylating reagent such as iodomethane or trifluoromethanesulfonic acid methyl ester, in the presence of a base, e.g., sodium hydrogencarbonate or potassium hydrogencarbonate, in a solvent such as methanol or acetonitrile, at temperatures between 0° C. and 60° C.

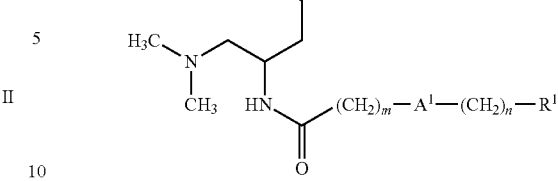

Compounds of formula II are synthesized from the corresponding esters 1 ($R^p$=methyl, ethyl, benzyl), using methods known in the art. Especially preferred are compounds 1 with $R^p$=benzyl, which can be converted to II by hydrogenation at a pressure of 1 to 10 bar, using a suitable catalyst, e.g., palladium on activated charcoal, in a solvent such as methanol or ethanol, at temperature between 0° C. to 50° C. Alternatively, esters 1 can be transformed into II by base-catalyzed hydrolysis, using reagents such as lithium hydroxide, sodium hydroxide, potassium hydroxide, in solvents such as water, methanol, ethanol, tetrahydrofuran, or mixtures thereof, at temperatures between 0° C. and 100° C.

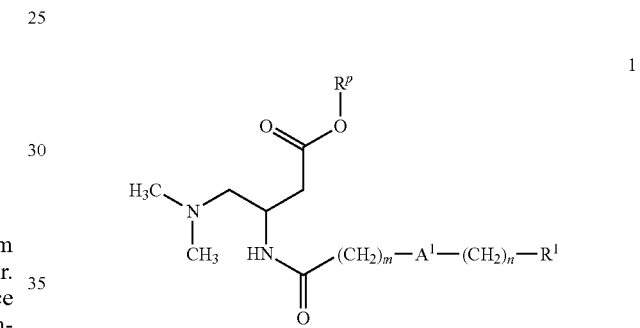

Alternatively, compounds of formula II, wherein $A^1$ is a bond and n is 2, can also be synthesized from ester 2 (in the case where $R^p$ is benzyl) by hydrogenation as described above, whereby a double bond eventually adjacent to $R^1$ as a result of the synthetic protocol used (see below) is also reduced. In the case where $R^p$ is methyl, ethyl, or benzyl, the transformation of 2 into (II) can also be accomplished in two steps as follows: In a first step the aforementioned double bond is reduced using triethysilane and trifluoroacetic acid in an inert solvent such as toluene or dichloromethane. In the second step the ester group is hydrolyzed, using reagents such as lithium hydroxide, sodium hydroxide, potassium hydroxide, in solvents such as water, methanol, ethanol, tetrahydrofuran, or mixtures thereof, at temperatures between 0° C. and 100° C.

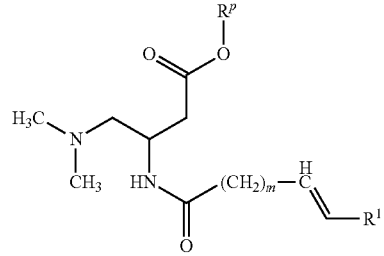

The compounds of formula 1 are synthesized from 3-amino-4-dimethylamino-butyrate 3

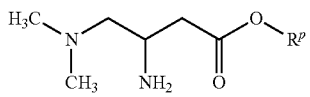

and carboxylic acid 4

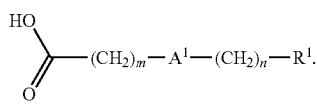

This can be carried out under conditions well known to the person skilled in the art. For example, the reaction can conveniently be carried out by mixing carboxylic acid 4 with amine 3 in aprotic solvents such as dichloromethane, tetrahydrofuran, N,N-dimethylformamide, N-methylpyrrolidinone and mixtures thereof at temperatures between 0° C. and 60° C. in the presence or absence of a base such as triethylamine or N,N-diisopropylethylamine, and a condensing agent. Appropriate condensing agents are selected for example from O-(7-benzotriazol-1-yl)-N,N,N',N'-tetramethyluronium-tetrafluoroborate (TBTU), O-(7-azabenzotriazol-1-yl)-N,N,N',N'-tetramethyluronium-hexafluorophophate (HATU), N,N'-dicyclohexylcarbodiimide, 1-(3-dimethylamino-propyl)-3-ethyl-carbodiimide hydrochloride, O-(benzotriazol-1-yl)-N,N,N',N'-tetramethyluronium hexafluoro-phosphate, bromo-tris-pyrrolidino-phosphonium hexafluorophosphate or others well known to the person skilled in the art.

Alternatively, such reactions can be performed in two steps involving first formation of the acyl halide derivative of 4 and subsequent coupling reaction with amine 3 in the presence of a base. Typically employed reagents for the formation of the acyl chloride are thionyl chloride, phosphorus pentachloride, oxalyl chloride or cyanuric chloride, and the reaction is generally conducted in the absence of a solvent or in the presence of an aprotic solvent like dichloromethane, toluene or acetone. A base can optionally be added, like for intermediate pyridine, triethylamine, diisopropylethylamine or 4-methylmorpholine. The obtained acyl chloride can be isolated or reacted as such with an amine 3 in an aprotic solvent, like dichloromethane, tetrahydrofuran or acetone, in the presence of a base. Typical bases are triethylamine, 4-methylmorpholine, pyridine, diisopropylethylamine or dimethylaminopyridine or mixtures thereof.

Alternatively, such reactions can be performed in two steps involving first formation of a mixed anhydride derivative of 4 obtained by reaction with a reagent such as ethyl chloroformate, isobutyl chloroformate or acetic anhydride, and subsequent reaction with amine 3 as described above.

Compounds of formula 2 are synthesized from 3-amino-4-dimethylaminobutyrate 3 and carboxylic acid 5, in analogy to 1.

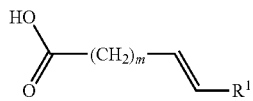

The synthesis of 3-amino-4-dimethylaminobutyrate 3 is highlighted in scheme 1 and starts from commercially available N-protected aspartic acid monoester 7. $R^p$ is methyl, ethyl, or benzyl, with benzyl being especially preferred.

SCHEME 1

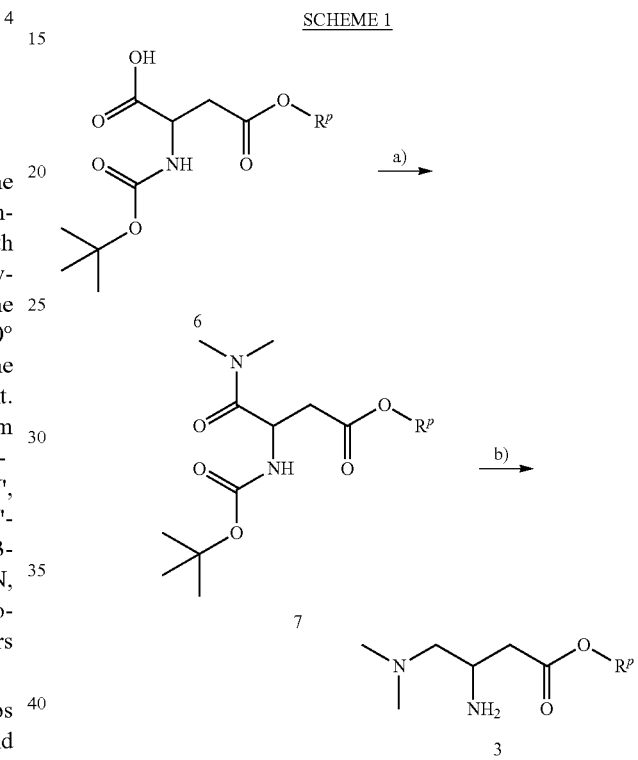

In step a, scheme 1, carboxylic acid 6 is reacted with dimethylamine to the N,N-dimethylamide derivative 7, using reagents and methods as described for the reaction of carboxylic acid 4 with amine 3.

In step b, scheme 1, N,N-dimethylamide 7 is converted to dimethylamine derivative 3 by reduction and subsequent removal of the tert-butoxycarbonyl protective group. Preferred reagents for the reduction are borane-tetrahydrofuran complex or borane-dimethylsulfide complex, in an aprotic solvent such as tetrahydrofuran, at temperatures between −20° C. and 80° C. Removal of the tert-butoxycarbonyl group is accomplished in an acidic environment, using hydrochloric acid or sulfuric acid, in solvents such as ethanol, methanol, water or mixtures thereof, at temperatures between 0° C. and 20° C.

Carboxylic acids 4 are either commercially available or can be produced as outlined in schemes 2 to 7.

When $R^1$ is as described above and $A^2$ is oxygen, carboxylic acids 5 can be produced as described in scheme 2, where X is a leaving group such as bromine, iodine, or methanesulfonyloxy and PG is an optional protective group, e.g., tetrahydropyran-2-yl.

SCHEME 2

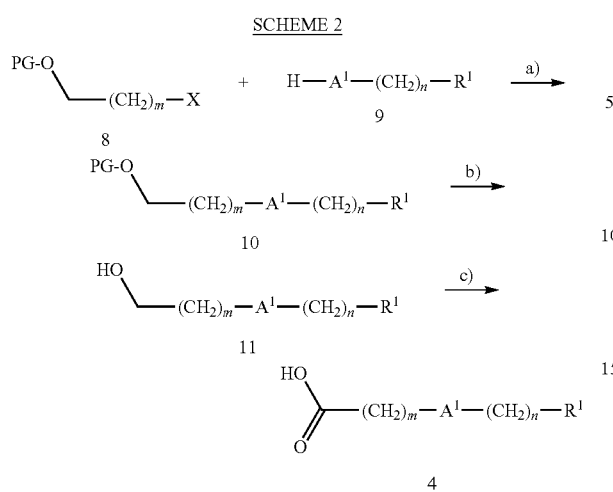

In step a, scheme 2, compound 9 is alkylated with optionally protected w-halo or w-sulfonyloxy alcohol 8, leading to 10. The reaction is performed in a solvent such as ethanol, acetonitrile, or N,N-dimethylformamide, in the presence of a base, e.g., potassium carbonate, sodium hydroxide, potassium tert-butylate, or sodium hydride, at temperatures between 0° C. and 100° C.

In optional step b (i.e., in the case where PG≠H), the protective group of 10 is removed, leading to alcohol 11. In the case of PG=tetrahydropyran-2-yl, this reaction is accomplished using an acid catalyst such as hydrochloric acid, toluene-4-sulfonic acid, or pyridinium toluene-4-sulfonate, in a solvent such as water, methanol, or ethanol, at temperatures between 0° C. and 100° C.

In step c, scheme 2, alcohol 11 is oxidized to carboxylic acid 4. Typically employed reagents and conditions for the oxidation of alcohol 11 include pyridinium dichromate, chromium(VI)oxide, or potassium permanganate. This oxidation of 11 to 4 is also possible for alcohols 11 in which $A^1$ is a bond.

Alternatively, alcohol 11 can be synthesized as outlined in scheme 3. $A^2$ is oxygen and R', m and n are as defined above. In this route diol 12 and compound 13 are reacted under Mitsunobu conditions using a phosphine, e.g., triphenylphosphine, and an azodicarboxylic acid diester, e.g., diethyl azodicarboxylate or diisopropyl azodicarboxylate, in a solvent such as tetrahydrofuran, dichloromethane, or toluene, at temperatures between 0° C. and 50° C., leading to 11.

SCHEME 3

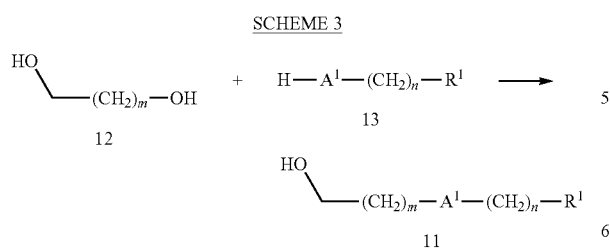

Alternatively, alcohol 11 can be synthesized as outlined in scheme 4. $A^1$ is oxygen and R', m and n are as defined above, X is a leaving group such as bromine, iodine, or methanesulfonyloxy. Thus, compound 14 is alkylated with halide or sulfonate 15. The reaction is performed in a solvent such as ethanol, acetonitrile, or N,N-dimethylform-amide, in the presence of a base, e.g., potassium carbonate, sodium hydroxide, potassium tert-butylate, or sodium hydride, at temperatures between 0° C. and 100° C.

SCHEME 4

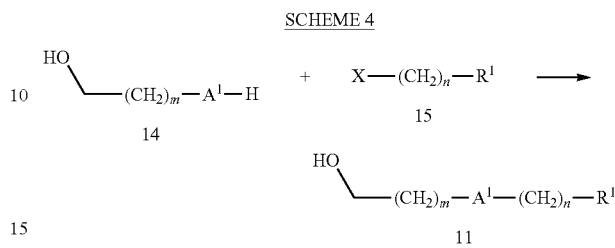

Acid 4 can also be synthesized as outlined in scheme 5. $A^1$ is oxygen and $R^1$, m and n are as defined above, X is a leaving group such as bromine, iodine, or methanesulfonyloxy. The alkylation of carboxylic acid 16 with halide or sulfonate 15 is performed in an analogous fashion to that of 14 with 15 (scheme 4).

SCHEME 5

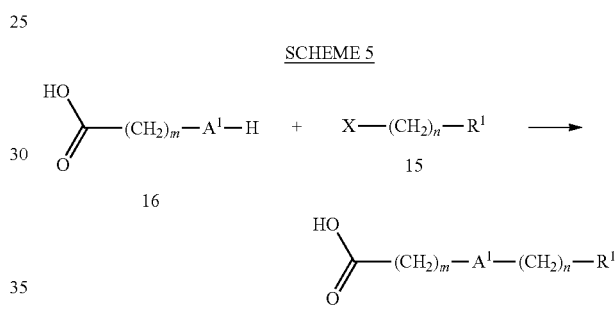

Unsaturated acids of general formula 5 can be synthesized as outlined in scheme 6. $R^1$ and m are as defined above, $R^a$ is lower alkyl, e.g., methyl or ethyl.

SCHEME 6

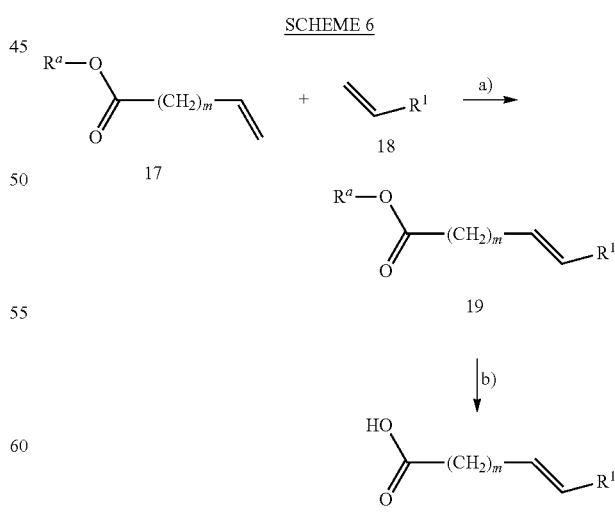

In step a, scheme 6, unsaturated ester 17 is reacted with styrene derivative 18 in an alkene cross-metathesis reaction, leading to 19. This reaction is carried out in an inert solvent, such as dichloromethane or toluene and requires a suitable catalyst, e.g., dichloro(1,3-dimesityl-4,5-dihydroimidazol-2-ylidene)(phenylmethylene)(tricyclohexyl-phosphine)ruthenium, at temperatures between 20° C. and 100° C.

In step b, scheme 6, ester 19 is converted to acid 5 by base-catalyzed hydrolysis, using reagents such as lithium hydroxide, sodium hydroxide, potassium hydroxide, in solvents such as water, methanol, ethanol, tetrahydrofuran, or mixtures thereof, at temperatures between 0° C. and 100° C.

Alternatively, unsaturated acids of formula 5 can be synthesized as outlined in scheme 7. $R^1$ and m are as defined above.

SCHEME 7

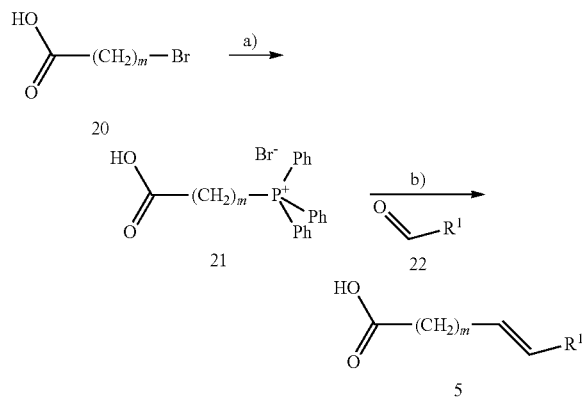

In step a, scheme 7, ω-bromoacid 20 is reacted with triphenylphosphine, leading to phosphonium salt 21. This reaction is carried out in an inert solvent such as toluene, at temperatures between 20° C. and 110° C.

In step b, scheme 7, phosphonium salt 21 is reacted with aldehyde 22, leading to 5. This reaction is carried out in the presence of a base, e.g., sodium hydride, n-butyllithium, or potassium tert-butylate, in a solvent such as diethyl ether or tetrahydrofuran, at temperatures between −20° C. and 50° C.

As described above, the novel compounds of formula I of the present invention have been found to inhibit carnitine palmitoyl transferase 2 (CPT2) activity. The compounds of the present invention can therefore be used in the treatment and/or prophylaxis of diseases that are modulated by CPT2 inhibitors, particularly diseases that are related to hyperglycemia and/or glucose tolerance disorders. Such diseases include e.g. diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

The invention therefore also relates to pharmaceutical compositions comprising a compound of formula I as defined above and a pharmaceutically acceptable carrier and/or adjuvant.

The invention also embraces compounds of formula I as described above for use as therapeutically active substances, especially as therapeutically active substances for the treatment and/or prophylaxis of diseases which are modulated by CPT2 inhibitors, particularly for use as therapeutically active substances for the treatment and/or prophylaxis of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure.

In another preferred embodiment, the invention relates to a method for the therapeutic and/or prophylactic treatment of diseases which are modulated by CPT2 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound of formula I as defined above to a human being or animal.

The invention also relates to the use of compounds of formula I as described above for the preparation of medicaments for the therapeutic and/or prophylactic treatment of diseases which are modulated by CPT2 inhibitors, particularly for the therapeutic and/or prophylactic treatment of hyperglycemia, glucose tolerance disorders, diabetes and associated pathologies, non insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure. Such medicaments comprise a compound of formula I as described above.

Prevention and/or treatment of hyperglycemia and non insulin dependent diabetes mellitus is the preferred use.

The following tests were carried out in order to determine the activity of the compounds of the present invention. Background information on the performed assays can be found in: Jackson et al., 1999, Biochem. J. 341, 483-489 and Jackson et al., 2000, J. Biol. Chem. 275, 19560-19566.

Human and rat CPT2- and liver CPT1 cDNAs, and human muscle CPT1 cDNA were subcloned in pGAPZB or pGAPZA, respectively. These plasmids were used to transform P. pastoris strain X-33 via electroporation after the preparation of electrocompetent cells. High copy number clones were selected where necessary using 0.5 or 1 mg/ml Zeocin. Cultures for activity measurements were induced for 16 h in YPD medium (1% yeast extract, 2% peptone, 2% glucose). Crude cell extracts were prepared by disrupting the cells with glass beads or French Press, depending on fermenter sizes. After centrifugation, the cell-free extracts were resuspended in cell breaking buffer (50 mM Tris, pH7.4, 100 mM KCl, 1 mM EDTA) in the presence of a protease inhibitor cocktail, before aliquoting and freezing at −20° C.

CPT activity was measured using a spectrophotometric assay using 5,5'-dithio-bis-(2-nitrobenzoic acid) (DTNB) also called Ellman's reagent. The HS-CoA released on the formation of acylcarnitine from carnitine (500 μM) and palmitoyl-CoA (80 μM) reduced DTNB (300 μM) forming 5-mercapto-2-nitrobenzoic acid which absorbed at 410 nm with a molar extinction coefficient of 13600 $M^{-1} \cdot cm^{-1}$. The assay buffer contained 120 mM KCl, 25 mM Tris, pH 7.4, 1 mM EDTA. This assay was used for the identification of CPT inhibitors, particularly/preferentially CPT2-selective inhibitors, versus the liver and muscle CPT1 isoforms.

The compounds according to formula I preferably have an $IC_{50}$ value (CPT2) below 10 μM, preferably 1 nM to 10 μM, more preferably 1 nM to 1 μM. The following table shows data for some examples.

| Example | hCPT2 inhibition IC$_{50}$ [µmol/l] | hL-CPT1 inhibition IC$_{50}$ [µmol/l] |
|---|---|---|
| 1 | 0.0732 | 2.190 |
| 2 | 0.1247 | 5.63 |
| 3 | 0.2981 | 1.122 |
| 6 | 0.0321 | 4.343 |
| 7 | 0.0323 | 2.249 |
| 8 | 0.0537 | 7.195 |
| 9 | 0.0012 | 1.091 |
| 12 | 0.041 | >10 |
| 15 | 0.0294 | 3.248 |
| 18 | 0.0145 | 0.621 |
| 24 | 0.0212 | 3.976 |
| 25 | 0.1246 | 3.066 |
| 26 | 0.0081 | 1.816 |
| 28 | 0.0202 | 0.8536 |
| 31 | 0.5378 | 1.375 |
| 32 | 0.2462 | 2.373 |
| 33 | 0.4863 | 6.081 |
| 34 | 0.0166 | 0.4269 |

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on the severity of the disease and the precise pharmacokinetic profile the compound could be administered with one or several daily dosage units, e.g. in 1 to 3 dosage units.

The pharmaceutical preparations conveniently contain about 1 to 500 mg, preferably 1 to 200 mg, of a compound of formula I.

The following examples serve to illustrate the present invention in more detail. They are, however, not intended to limit its scope in any manner.

EXAMPLES

Abbreviations

HPLC=high pressure liquid chromatography, m/e=mass to charge ratio as measured by mass spectrometry (MS).

Intermediate 1

(R)-3-[8-(3,4-Difluoro-benzyloxy)-octanoylamino]-4-dimethylamino-butyric acid

Step 1: A solution of 1,8-octanediol (300 mg, 2.05 mmol) in tetrahydrofuran/N,N-dimethylformamide 2:1 (3 mL) was added dropwise at 0° C. to a suspension of sodium hydride (60% dispersion in mineral oil, 90 mg, 2.3 mmol) in N,N-dimethylformamide (1.5 mL), then after 2 h 3,4-difluorobenzyl bromide (445 mg, 2.15 mmol) was added. After 4 h the reaction mixture was partitioned between water and ethyl acetate. The organic layer was washed with brine, dried over sodium sulfate, filtered, and evaporated. Chromatography (SiO$_2$, heptane-ethyl acetate gradient) afforded 8-(3,4-difluoro-benzyloxy)-octan-1-ol (258 mg, 46%). Colorless oil, m/e=273.3 ([M+H]$^+$).

Step 2: Pyridinium dichromate (1.23 g, 3.27 mmol) was added at 0° C. to a solution of 8-(3,4-difluoro-benzyloxy)-octan-1-ol (254 mg, 0.93 mmol) in N,N-dimethylform-amide (2 mL). The reaction mixture was allowed to reach room temperature over 16 h, then partitioned between water and ethyl acetate. The organic layer was washed with brine, dried over sodium sulfate, filtered, and evaporated. Chromatography (SiO$_2$, heptane-[ethyl acetate/formic acid 100:1] gradient) afforded 8-(3,4-difluoro-benzyloxy)-octanoic acid (162 mg, 61%). Colorless oil, m/e=285.1 ([M−H]$^-$).

Step 3: A solution of 8-(3,4-difluoro-benzyloxy)-octanoic acid (153 mg, 0.53 mmol), N,N-diisopropylethylamine (414 mg, 3.21 mmol), and O-(7-azabenzotriazol-1-yl)-N,N,N',N'-tetramethyluronium-hexafluorophosphate (244 mg, 0.64 mmol) in N,N-dimethylformamide was stirred for 1 h at room temperature, then a solution of (R)-3-amino-4-dimethylamino-butyric acid benzyl ester dihydrochloride (198 mg, 0.64 mmol) in N,N-dimethylformamide (1 mL) was added. The reaction mixture was stirred for 16 h at room temperature, then evaporated. Chromatography (SiO$_2$, dichloromethane-[dichloromethane/methanol/25% aq. ammonia solution 110:10:1] gradient) produced (R)-3-[8-(3,4-difluoro-benzyloxy)-octanoylamino]-4-dimethylamino-butyric acid benzyl ester (136 mg, 50%). Light yellow oil, m/e=505.4 ([M+H]$^+$).

Step 4: A solution of (R)-3-[8-(3,4-difluoro-benzyloxy)-octanoylamino]-4-dimethylamino-butyric acid benzyl ester (125 mg, 0.25 mmol) was hydrogenated under atmospheric pressure in the presence of palladium (10% on activated charcoal, 30 mg). After 30 min, the catalyst was filtered off and the filtrate concentrated and dried to afford (R)-3-[8-(3,4-difluoro-benzyloxy)-octanoylamino]-4-dimethylamino-butyric acid (96 mg, 89%). Light yellow oil, m/e=413.2 ([M−H]$^-$).

Preparation of (R)-3-amino-4-dimethylamino-butyric acid benzyl ester dihydrochloride a) Triethylamine (2.8 mL, 20.0 mmol) was added at 0° C. to a solution of Boc-D-aspartic acid 4-benzyl ester (5.00 g, 15.0 mmol) in dichloromethane, then ethyl chloroformate (1.91 mL, 20.0 mmol) was added dropwise. The reaction mixture was stirred for 1 h at 0° C., then a solution of dimethylamine hydrochloride (2.65 g, 32.0 mmol) and triethylamine (4.53 mL, 32.0 mmol) in dichloromethane (100 mL) were added dropwise. The reaction mixture was allowed to reach room temperature over 16 h, then washed with brine, and concentrated. Chromatography (SiO$_2$; heptane-ethyl acetate gradient) produced (R)-3-tert-butoxycarbonylamino-N,N-dimethyl-succinamic acid benzyl ester (3.77 g, 70%). Colorless oil, m/e=351.4 ([M+H]$^+$).

b) Borane-dimethyl sulfide complex (1.57 mL, 3.14 mmol) was added dropwise at 0° C. to a solution of (R)-3-tert-butoxycarbonylamino-N,N-dimethyl-succinamic acid benzyl ester (500 mg, 1.43 mmol). The reaction mixture was warmed to room temperature and heated at reflux for 3 hours, then cooled to 0° C. and treated dropwise with 6 M aq. hydrochloric acid solution (0.68 mL, 4.1 mmol). The reaction mixture was allowed to warm to room temperature and concentrated in vacuo. Residual water was azeotroped with toluene and concentrated under high vacuum to afford (R)-3-amino-4-dimethylamino-butyric acid benzyl ester dihydrochloride (384 mg, 87%). White solid, m/e=237.4 ([M+H]$^+$).

Intermediate 2

(R)-3-[8-(2,5-Difluoro-benzyloxy)-octanoylamino]-4-dimethylamino-butyric acid

The title compound, m/e=413.3 ([M−H]$^-$), was produced in analogy with intermediate 1, steps 1 to 4. Thus, 1,8-octanediol was alkylated in step 1 with 2,5-difluorobenzyl bromide, leading to 8-(2,5-difluoro-benzyloxy)-octan-1-ol, which was oxidized in step 2 to 8-(2,5-difluoro-benzyloxy)-octanoic acid. This was coupled in step 3 with (R)-3-amino-4-dimethylamino-butyric acid benzyl ester dihydrochloride to produce (R)-3-[8-(2,5-difluoro-benzyloxy)-octanoylamino]-4-dimethylamino-butyric acid benzyl ester, which was hydrogenated in step 4.

Intermediate 3

(R)-3-[8-(2,4-Difluoro-benzyloxy)-octanoylamino]-4-dimethylamino-butyric acid

The title compound, m/e=413.1 ([M−H]$^-$), was produced in analogy with intermediate 1, steps 1 to 4. Thus, 1,8-octanediol was alkylated in step 1 with 2,4-difluorobenzyl bromide, leading to 8-(2,4-difluoro-benzyloxy)-octan-1-ol, which was oxidized in step 2 to 8-(2,4-difluoro-benzyloxy)-octanoic acid. This was coupled in step 3 with (R)-3-amino-4-dimethylamino-butyric acid benzyl ester dihydrochloride to produce (R)-3-[8-(2,4-difluoro-benzyloxy)-octanoylamino]-4-dimethylamino-butyric acid benzyl ester, which was hydrogenated in step 4.

Intermediate 4

(R)-4-Dimethylamino-3-[8-(2,3,4-trifluoro-benzyloxy)-octanoylamino]-butyric acid The title compound, m/e=432.5 ([M+H]$^+$), was produced in analogy with intermediate 1, steps 1 to 4. Thus, 1,8-octanediol was alkylated in step 1 with 2,3,4-trifluorobenzyl bromide, leading to 8-(2,3,4-trifluoro-benzyloxy)-octan-1-ol, which was oxidized in step 2 to 8-(2,3,4-trifluoro-benzyloxy)-octanoic acid. This was coupled in step 3 with (R)-3-amino-4-dimethylamino-butyric acid benzyl ester dihydrochloride to produce (R)-3-[8-(2,3,4-trifluoro-benzyloxy)-octanoylamino]-4-dimethylamino-butyric acid benzyl ester, which was hydrogenated in step 4.

Intermediate 5

(R)-4-Dimethylamino-3-(8-pentafluorophenylmethoxy-octanoylamino)-butyric acid

The title compound, m/e=467.5 ([M−H]$^-$), was produced in analogy with intermediate 1, steps 1 to 4. Thus, 1,8-octanediol was alkylated in step 1 with pentafluorobenzyl bromide, leading to 8-(pentafluoro-benzyloxy)-octan-1-ol, which was oxidized in step 2 to 8-(pentafluoro-benzyloxy)-octanoic acid. This was coupled in step 3 with (R)-3-amino-4-dimethylamino-butyric acid benzyl ester dihydrochloride to produce (R)-3-[8-(pentafluoro-benzyloxy)-octanoylamino]-4-dimethylamino-butyric acid benzyl ester, which was hydrogenated in step 4.

Intermediate 6

(R)-4-Dimethylamino-3-[8-(4-trifluoromethyl-benzyloxy)-octanoylamino]-butyric acid The title compound, m/e=445.6 ([M−H]$^-$), was produced in analogy with intermediate 1, steps 1 to 4. Thus, 1,8-octanediol was alkylated in step 1 with 4-trifluoromethyl-benzyl bromide, leading to 8-(4-trifluoromethyl-benzyloxy)-octan-1-ol, which was oxidized in step 2 to 8-(4-trifluoromethyl-benzyloxy)-octanoic acid. This was coupled in step 3 with (R)-3-amino-4-dimethylamino-butyric acid benzyl ester dihydrochloride to produce (R)-3-[8-(4-trifluoromethyl-benzyloxy)-octanoylamino]-4-dimethylamino-butyric acid benzyl ester, which was hydrogenated in step 4.

Intermediate 7

(R)-4-Dimethylamino-3-[8-(3-fluoro-4-trifluoromethyl-benzyloxy)-octanoylamino]-butyric acid The title compound, m/e=463.5 ([M−H]$^-$), was produced in analogy with intermediate 1, steps 1 to 4. Thus, 1,8-octanediol was alkylated in step 1 with 3-fluoro-4-trifluoromethyl-benzyl bromide, leading to 8-(3-fluoro-4-trifluoromethyl-benzyloxy)-octan-1-ol, which was oxidized in step 2 to 8-(3-fluoro-4-trifluoromethyl-benzyloxy)-octanoic acid. This was coupled in step 3 with (R)-3-amino-4-dimethylamino-butyric acid benzyl ester dihydrochloride to produce (R)-3-[8-(3-fluoro-4-trifluoromethyl-benzyloxy)-octanoylamino]-4-dimethylamino-butyric acid benzyl ester, which was hydrogenated in step 4.

Intermediate 8

(R)-4-Dimethylamino-3-[8-(4-methoxy-benzyloxy)-octanoylamino]-butyric acid

The title compound, m/e=407.6 ([M−H]⁻), was produced in analogy with intermediate 1, steps 1 to 4. Thus, 1,8-octanediol was alkylated in step 1 with 4-methoxy-benzyl bromide, leading to 8-(4-methoxy-benzyloxy)-octan-1-ol, which was oxidized in step 2 to 8-(4-methoxy-benzyloxy)-octanoic acid. This was coupled in step 3 with (R)-3-amino-4-dimethylamino-butyric acid benzyl ester dihydrochloride to produce (R)-3-[8-(4-methoxy-benzyloxy)-octanoylamino]-4-dimethylamino-butyric acid benzyl ester, which was hydrogenated in step 4.

Intermediate 9

(R)-3-[8-(Biphenyl-4-ylmethoxy)-octanoylamino]-4-dimethylamino-butyric acid

The title compound, m/e=455.3 ([M+H]⁺), was produced in analogy with intermediate 1, steps 1 to 4. Thus, 1,8-octanediol was alkylated in step 1 with 4-(bromomethyl)-biphenyl, leading to 8-(biphenyl-4-ylmethoxy)-octan-1-ol, which was oxidized in step 2 to 8-(biphenyl-4-ylmethoxy)-octanoic acid. This was coupled in step 3 with (R)-3-amino-4-dimethylamino-butyric acid benzyl ester dihydrochloride to produce (R)-3-[8-(biphenyl-4-ylmethoxy)-octanoylamino]-4-dimethylamino-butyric acid benzyl ester, which was hydrogenated in step 4.

Intermediate 10

(R)-4-Dimethylamino-3-[8-(2-fluoro-4-trifluoromethyl-benzyloxy)-octanoylamino]-butyric acid The title compound, m/e=463.1 ([M−H]⁻), was produced in analogy with intermediate 1, steps 1 to 4. Thus, 1,8-octanediol was alkylated in step 1 with 2-fluoro-4-trifluoromethyl-benzyl bromide, leading to 8-(2-fluoro-4-trifluoromethyl-benzyloxy)-octan-1-ol, which was oxidized in step 2 to 8-(2-fluoro-4-trifluoromethyl-benzyloxy)-octanoic acid. This was coupled in step 3 with (R)-3-amino-4-dimethylamino-butyric acid benzyl ester dihydrochloride to produce (R)-3-[8-(2-fluoro-4-trifluoromethyl-benzyloxy)-octanoylamino]-4-dimethylamino-butyric acid benzyl ester, which was hydrogenated in step 4.

Intermediate 11

(R)-4-Dimethylamino-3-[8-(2,3,5,6-tetrafluoro-4-methoxy-benzyloxy)-octanoylamino]-butyric acid The title compound, m/e=479.4 ([M−H]⁻), was produced in analogy with intermediate 1, steps 1 to 4. Thus, 1,8-octanediol was alkylated in step 1 with 2,3,5,6-tetrafluoro-4-methoxy-benzyl bromide, leading to 8-(2,3,5,6-tetrafluoro-4-methoxy-benzyloxy)-octan-1-ol, which was oxidized in step 2 to 8-(2,3,5,6-tetrafluoro-4-methoxy-benzyloxy)-octanoic acid. This was coupled in step 3 with (R)-3-amino-4-dimethylamino-butyric acid benzyl ester dihydrochloride to produce (R)-3-[8-(2,3,5,6-tetrafluoro-4-methoxy-benzyloxy)-octanoylamino]-4-dimethylamino-butyric acid benzyl ester, which was hydrogenated in step 4.

Intermediate 12

(R)-4-Dimethylamino-3-[8-(naphthalen-1-ylmethoxy)-octanoylamino]-butyric acid

The title compound, m/e=427.1 ([M−H]⁻), was produced in analogy with intermediate 1, steps 1 to 4. Thus, 1,8-octanediol was alkylated in step 1 with 1-bromomethyl-naphthalene, leading to 8-(naphthalen-1-ylmethoxy)-octan-1-ol, which was oxidized in step 2 to 8-(naphthalen-1-ylmethoxy)-octanoic acid. This was coupled in step 3 with (R)-3-amino-4-dimethylamino-butyric acid benzyl ester dihydrochloride to produce (R)-3-[8-(naphthalen-1-ylmethoxy)-octanoylamino]-4-dimethylamino-butyric acid benzyl ester, which was hydrogenated in step 4.

Intermediate 13

(R)-3-(8-Benzyloxy-octanoylamino)-4-dimethylamino-butyric acid

The title compound, m/e=377.6 ([M−H]⁻), was produced in analogy with intermediate 1, steps 1 to 4. Thus, 1,8-octanediol was alkylated in step 1 with benzyl bromide, leading to 8-benzyloxy-octan-1-ol, which was oxidized in step 2 to 8-benzyloxy-octanoic acid. This was coupled in step 3 with (R)-3-amino-4-dimethylamino-butyric acid benzyl ester dihydrochloride to produce (R)-3-[8-benzyloxy)-octanoylamino]-4-dimethylamino-butyric acid benzyl ester, which was hydrogenated in step 4.

Intermediate 14

(R)-4-Dimethylamino-3-[8-(2-fluoro-benzyloxy)-octanoylamino]-butyric acid

The title compound, m/e=397.4 ([M+H]⁺), was produced in analogy with intermediate 1, steps 1 to 4. Thus, 1,8-octanediol was alkylated in step 1 with 2-fluorobenzyl bromide, leading to 8-(2-fluoro-benzyloxy)-octan-1-ol, which was oxidized in step 2 to 8-(2-fluoro-benzyloxy)-octanoic acid. This was coupled in step 3 with (R)-3-amino-4-dimethylamino-butyric acid benzyl ester dihydrochloride to produce (R)-3-[8-(2-fluoro-benzyloxy)-octanoylamino]-4-dimethylamino-butyric acid benzyl ester, which was hydrogenated in step 4.

Intermediate 15

(R)-4-Dimethylamino-3-[8-(3-fluoro-benzyloxy)-octanoylamino]-butyric acid

The title compound, m/e=397.4 ([M+H]⁺), was produced in analogy with intermediate 1, steps 1 to 4. Thus, 1,8-octanediol was alkylated in step 1 with 3-fluorobenzyl bromide, leading to 8-(3-fluoro-benzyloxy)-octan-1-ol, which was oxidized in step 2 to 8-(3-fluoro-benzyloxy)-octanoic acid. This was coupled in step 3 with (R)-3-amino-4-dimethylamino-butyric acid benzyl ester dihydrochloride to produce (R)-3-[8-(3-fluoro-benzyloxy)-octanoylamino]-4-dimethylamino-butyric acid benzyl ester, which was hydrogenated in step 4.

Intermediate 16

(R)-4-Dimethylamino-3-[8-(4-fluoro-benzyloxy)-octanoylamino]-butyric acid

The title compound, m/e=397.4 ([M+H]$^+$), was produced in analogy with intermediate 1, steps 1 to 4. Thus, 1,8-octanediol was alkylated in step 1 with 4-fluorobenzyl bromide, leading to 8-(4-fluoro-benzyloxy)-octan-1-ol, which was oxidized in step 2 to 8-(4-fluoro-benzyloxy)-octanoic acid. This was coupled in step 3 with (R)-3-amino-4-dimethylamino-butyric acid benzyl ester dihydrochloride to produce (R)-3-[8-(4-fluoro-benzyloxy)-octanoylamino]-4-dimethylamino-butyric acid benzyl ester, which was hydrogenated in step 4.

Intermediate 17

(R)-3-[8-(2,3-Difluoro-benzyloxy)-octanoylamino]-4-dimethylamino-butyric acid

The title compound, m/e=415.5 ([M+H]$^+$), was produced in analogy with intermediate 1, steps 1 to 4. Thus, 1,8-octanediol was alkylated in step 1 with 2,3-difluorobenzyl bromide, leading to 8-(2,3-difluoro-benzyloxy)-octan-1-ol, which was oxidized in step 2 to 8-(2,3-difluoro-benzyloxy)-octanoic acid. This was coupled in step 3 with (R)-3-amino-4-dimethylamino-butyric acid benzyl ester dihydrochloride to produce (R)-3-[8-(2,3-difluoro-benzyloxy)-octanoylamino]-4-dimethylamino-butyric acid benzyl ester, which was hydrogenated in step 4.

Intermediate 18

(R)-4-Dimethylamino-3-(10-phenyl-decanoylamino)-butyric acid

The title compound, m/e=377.3 ([M+H]$^+$), was produced in analogy with intermediate 1, steps 3 and 4. Thus, commercially available 10-phenyldecanoic acid was coupled in step 3 with (R)-3-amino-4-dimethylamino-butyric acid benzyl ester dihydrochloride to produce (R)-4-dimethylamino-3-(10-phenyl-decanoylamino)-butyric acid benzyl ester, which was hydrogenated in step 4.

Intermediate 19

(S)-4-Dimethylamino-3-(10-phenyl-decanoylamino)-butyric acid

The title compound, m/e=377.5 ([M+H]$^+$), was produced in analogy with intermediate 1, steps 3 and 4. Thus, commercially available 10-phenyldecanoic acid was coupled in step 3 with (S)-3-amino-4-dimethylamino-butyric acid benzyl ester dihydrochloride to produce (S)-4-dimethylamino-3-(10-phenyl-decanoylamino)-butyric acid benzyl ester, which was hydrogenated in step 4.

(S)-3-Amino-4-dimethylamino-butyric acid benzyl ester dihydrochloride was prepared in analogy with (R)-3-amino-4-dimethylamino-butyric acid benzyl ester dihydrochloride (intermediate 1), starting from Boc-L-aspartic acid 4-benzyl ester.

Intermediate 20

(R)-4-Dimethylamino-3-[10-(2-fluoro-phenyl)-decanoylamino]-butyric acid

Step 1: To a solution of 9-decenoic acid ethyl ester (*Tetrahedron* 2003, 59, 7973; 500 mg, 2.53 mmol) and 2-fluorostyrene (617 mg, 5.05 mmol) in dichloromethane (12.5 mL) was added dichloro(1,3-dimesityl-4,5-dihydroimidazol-2-ylidene)(phenylmethylene)(tri-cyclohexylphosphine)ruthenium (107 mg, 0.13 mmol). The mixture was flushed with nitrogen and sealed in a pressure tube, then heated at 40° C. for 18 h. After cooling and evaporation of the solvent, the product was purified by chromatography (SiO$_2$, heptane-dichloromethane 3:1) to afford 10-(2-fluoro-phenyl)-dec-9-enoic acid ethyl ester (420 mg, 57%).

Step 2: To a solution of 10-(2-fluoro-phenyl)-dec-9-enoic acid ethyl ester (420 mg, 1.44 mmol) in tetrahydrofuran (2 mL) was added 2 M aq. lithium hydroxide solution (2 mL, 4 mmol). The reaction mixture was stirred at room temperature for 16 h, then partitioned between 1 M aq. hydrochloric acid solution and ethyl acetate. The organic layer was dried over magnesium sulfate, filtered, and evaporated, to afford 10-(2-fluoro-phenyl)-dec-9-enoic acid (250 mg, 66%).

Step 3: In analogy with intermediate 22, step 3, 10-(2-fluoro-phenyl)-dec-9-enoic acid was converted to 10-(2-fluoro-phenyl)-dec-9-enoyl chloride, then reacted with (R)-3-amino-4-dimethylamino-butyric acid benzyl ester dihydrochloride, leading to (R)-4-dimethylamino-3-[10-(2-fluoro-phenyl)-dec-9-enoylamino]-butyric acid benzyl ester.

Step 4: Hydrogenation of (R)-4-dimethylamino-3-[10-(2-fluoro-phenyl)-dec-9-enoylamino]-butyric acid benzyl ester in analogy with intermediate 1, step 4 produced (R)-4-dimethylamino-3-[10-(2-fluoro-phenyl)-decanoylamino]-butyric acid, m/e=395.2 ([M+H]$^+$).

Intermediate 21

(R)-4-Dimethylamino-3-[10-(2,5-dimethyl-phenyl)-decanoylamino]-butyric acid

The title compound, m/e=405.4 ([M+H]$^+$), was produced in analogy with intermediate 20, steps 1 to 4. Thus, 9-decenoic acid ethyl ester was reacted in step 1 with 2,5-dimethylstyrene, leading to 10-(2,5-dimethyl-phenyl)-dec-9-enoic acid ethyl ester, which was hydrolyzed in step 2 to 10-(2,5-dimethyl-phenyl)-dec-9-enoic acid. In step 3, this was converted to 10-(2,5-dimethyl-phenyl)-dec-9-enoyl chloride, then reacted with (R)-3-amino-4-dimethylamino-butyric acid benzyl ester dihydrochloride, leading to (R)-4-dimethylamino-3-[10-(2,5-dimethyl-phenyl)-dec-9-enoylamino]-butyric acid benzyl ester, which was hydrogenated in step 4.

Intermediate 22

(R)-4-Dimethylamino-3-[10-(2,6-dimethyl-phenyl)-decanoylamino]-butyric acid

Step 1: To a solution of 9-bromo-nonanoic acid (7.00 g, 29.5 mmol) in toluene (10 mL) was added triphenylphosphine (7.74 g, 29.5 mmol). The solution was sealed under nitrogen in a pressure tube and heated at 110° C. for 18 hours. On reaction completion two phases were observed. The toluene top layer was decanted from the crude product which was washed with toluene. (8-Carboxy-octyl)-triphenyl-phosphonium bromide (14.9 g) was obtained, which was directly used in the next step. White semisolid, m/e=419.3 ([M+H]$^+$).

Step 2: Sodium hydride (60% dispersion in mineral oil; 0.65 g, 16 mmol) was added portionwise at room temperature to a stirred solution of (8-carboxy-octyl)-triphenyl-phosphonium bromide (2.8 g, 5.6 mmol) in tetrahydrofuran (30 mL) at room temperature, then after 1 hour 2,6-dimethylbenzaldehyde (757 mg, 5.64 mmol) was added portionwise to the reaction mixture and the solution stirred for 2 days at room temperature. On reaction completion, water (10 ml) was added and the solution acidified to pH 3 with concentrated hydrochloric acid. The product was extracted with ethyl acetate, the organic layer dried over magnesium sulfate, filtered and evaporated. Chromatography (SiO$_2$, heptane-ethyl acetate 4:1) afforded 10-(2,6-dimethyl-phenyl)-dec-9-enoic acid as a colorless oil.

Step 3: A solution of 10-(2,6-dimethyl-phenyl)-dec-9-enoic acid (239 mg, 0.87 mmol), oxalyl chloride (0.11 mL, 1.3 mmol), and N,N-dimethylformamide (one drop) in dichloromethane (3 mL) was stirred at room temperature for 2 hours, then volatile material was removed by distillation to afford 10-(2,6-dimethyl-phenyl)-dec-9-enoyl chloride. This was redissolved in dichloromethane, then N,N-diisopropyl-ethylamine (140 mg, 1.04 mmol) was added dropwise, followed by (R)-3-amino-4-dimethylamino-butyric acid benzyl ester dihydrochloride. The reaction mixture was stirred at room temperature for 16 h, then washed with water. The organic layer was evaporated and the residue purified by preparative HPLC to afford (R)-4-dimethylamino-3-[10-(2,6-dimethyl-phenyl)-dec-9-enoylamino]-butyric acid benzyl ester.

Step 4: Hydrogenation of (R)-4-dimethylamino-3-[10-(2,5-dimethyl-phenyl)-dec-9-enoylamino]-butyric acid benzyl ester in analogy with intermediate 1, step 4 produced (R)-4-dimethylamino-3-[10-(2,6-dimethyl-phenyl)-decanoylamino]-butyric acid, m/e=405.3 ([M+H]$^+$).

Intermediate 23

(R)-4-Dimethylamino-3-[10-(4-methoxy-phenyl)-decanoylamino]-butyric acid

The title compound, m/e=407.3 ([M+H]$^+$), was produced in analogy with intermediate 20, steps 1 to 4. Thus, 9-decenoic acid ethyl ester was reacted in step 1 with 4-methoxystyrene, leading to 10-(4-methoxy-phenyl)-dec-9-enoic acid ethyl ester, which was hydrolyzed in step 2 to 10-(4-methoxy-phenyl)-dec-9-enoic acid. In step 3, this was converted to 10-(4-methoxy-phenyl)-dec-9-enoyl chloride, then reacted with (R)-3-amino-4-dimethylamino-butyric acid benzyl ester dihydrochloride, leading to (R)-4-dimethylamino-3-[10-(4-methoxy-phenyl)-dec-9-enoylamino]-butyric acid benzyl ester, which was hydrogenated in step 4.

Intermediate 24

(R)-4-Dimethylamino-3-(10-naphthalen-1-yl-decanoylamino)-butyric acid

The title compound, m/e=427.4 ([M+H]$^+$), was produced in analogy with intermediate 20, steps 1 to 4. Thus, 9-decenoic acid ethyl ester was reacted in step 1 with 1-vinylnaphthalene, leading to 10-(naphthalene-1-yl)-dec-9-enoic acid ethyl ester, which was hydrolyzed in step 2 to 10-(naphthalene-1-yl)-dec-9-enoic acid. In step 3, this was converted to 10-(naphthalene-1-yl)-dec-9-enoyl chloride, then reacted with (R)-3-amino-4-dimethylamino-butyric acid benzyl ester dihydrochloride, leading to (R)-4-dimethylamino-3-[10-(naphthalene-1-yl)-dec-9-enoylamino]-butyric acid benzyl ester, which was hydrogenated in step 4.

Intermediate 25

(R)-4-Dimethylamino-3-[10-(4-trifluoromethyl-phenyl)-decanoylamino]-butyric acid The title compound, m/e=445.1 ([M+H]$^+$), was produced in analogy with intermediate 20, steps 1 to 4. Thus, 9-decenoic acid ethyl ester was reacted in step 1 with 4-trifluoromethylstyrene, leading to 10-(4-trifluoromethyl-phenyl)-dec-9-enoic acid ethyl ester, which was hydrolyzed in step 2 to 10-(4-trifluoromethyl-phenyl)-dec-9-enoic acid. In step 3, this was converted to 10-(4-trifluoromethyl-phenyl)-dec-9-enoyl chloride, then reacted with (R)-3-amino-4-dimethylamino-butyric acid benzyl ester dihydrochloride, leading to (R)-4-dimethylamino-3-[10-(4-trifluoromethyl-phenyl)-dec-9-enoylamino]-butyric acid benzyl ester, which was hydrogenated in step 4.

Intermediate 26

(R)-4-Dimethylamino-3-[10-(3-fluoro-phenyl)-decanoylamino]-butyric acid

The title compound, m/e=395.3 ([M+H]$^+$), was produced in analogy with intermediate 20, steps 1 to 4. Thus, 9-decenoic acid ethyl ester was reacted in step 1 with 3-fluorostyrene, leading to 10-(3-fluoro-phenyl)-dec-9-enoic acid ethyl ester, which was hydrolyzed in step 2 to 10-(3-fluoro-phenyl)-dec-9-enoic acid. In step 3, this was converted to 10-(3-fluoro-phenyl)-dec-9-enoyl chloride, then reacted with (R)-3-amino-4-dimethylamino-butyric acid benzyl ester dihydrochloride, leading to (R)-4-dimethylamino-3-[10-(3-fluoro-phenyl)-dec-9-enoylamino]-butyric acid benzyl ester, which was hydrogenated in step 4.

Intermediate 27

(R)-3-[10-(2,3-Difluoro-phenyl)-decanoylamino]-4-dimethylamino-butyric acid

The title compound, m/e=413.3 ([M+H]$^+$), was produced in analogy with intermediate 22, steps 2 to 4. Thus 2,3-difluorobenzaldehyde was reacted in step 2 with (8-carboxy-octyl)-triphenyl-phosphonium bromide, leading to 10-(2,3-difluoro-phenyl)-dec-9-enoic acid. In step 3, this was converted to 10-(2,3-difluoro-phenyl)-dec-9-enoyl chloride, then reacted with (R)-3-amino-4-dimethylamino-butyric acid benzyl ester dihydrochloride, leading to (R)-4-dimethylamino-3-[10-(2,3-difluoro-phenyl)-dec-9-enoylamino]-butyric acid benzyl ester, which was hydrogenated in step 4.

Intermediate 28

(R)-4-Dimethylamino-3-(10-thiophen-3-yl-decanoylamino)-butyric acid

Step 1: Reaction of 3-thiophenecarboxaldehyde with (8-carboxy-octyl)-triphenyl-phosphonium bromide, in analogy with intermediate 22, step 2, produced 10-(thiophen-3-yl)-dec-9-enoic acid.

Step 2: In analogy with intermediate 22, step 3, 10-(thiophen-3-yl)-dec-9-enoic acid was converted to 10-(thiophen-3-yl)-dec-9-enoyl chloride, then reacted with (R)-3-amino-4-dimethylamino-butyric acid benzyl ester dihydrochloride, leading to (R)-4-dimethylamino-3-[10-(thiophen-3-yl)-dec-9-enoylamino]-butyric acid benzyl ester.

Step 3: Triethylsilane (0.23 mL, 1.43 mmol) and trifluoro-acetic acid (0.21 mL, 2.9 mmol) were added to a solution of 4-dimethylamino-3-(10-thiophen-3-yl-dec-9-enoylamino)-butyric acid benzyl ester (67 mg, 0.14 mmol) in toluene (8 mL). The reaction mixture was stirred at room temperature for 12 hours after which time the solution was added to cold saturated aq. sodium bicarbonate solution. The aqueous phase was separated and extracted twice with dichloromethane. The combined organics were dried over magnesium sulfate, filtered and concentrated in vacuo to afford 4-dimethylamino-3-(10-thiophen-3-yl-decanoylamino)-butyric acid benzyl ester (74 mg), m/e=473.3 ([M+H]⁺).

Step 4: Hydrolysis of 4-dimethylamino-3-(10-thiophen-3-yl-decanoylamino)-butyric acid benzyl ester, in analogy with intermediate 20, step 2, produced (R)-4-dimethylamino-3-(10-thiophen-3-yl-decanoylamino)-butyric acid, m/e=383.1 ([M+H]⁺).

Intermediate 29

(R)-4-Dimethylamino-3-(6-phenyl-hexanoylamino)-butyric acid

The title compound, m/e=321.3 ([M+H]⁺), was produced in analogy with intermediate 1, steps 3 and 4. Thus, commercially available 6-phenylhexanoic acid was coupled in step 3 with (R)-3-amino-4-dimethylamino-butyric acid benzyl ester dihydrochloride to produce (R)-4-dimethylamino-3-(6-phenyl-hexanoylamino)-butyric acid benzyl ester, which was hydrogenated in step 4.

Intermediate 30

(R)-4-Dimethylamino-3-(7-phenyl-heptanoylamino)-butyric acid

The title compound, m/e=335.4 ([M+H]⁺), was produced in analogy with intermediate 1, steps 3 and 4. Thus, commercially available 7-phenylheptanoic acid was coupled in step 3 with (R)-3-amino-4-dimethylamino-butyric acid benzyl ester dihydrochloride to produce (R)-4-dimethylamino-3-(7-phenyl-heptanoylamino)-butyric acid benzyl ester, which was hydrogenated in step 4.

Intermediate 31

(R)-4-Dimethylamino-3-(8-phenyl-octanoylamino)-butyric acid

The title compound, m/e=347.4 ([M−H]⁻), was produced in analogy with intermediate 1, steps 3 and 4. Thus, commercially available 8-phenyloctanoic acid was coupled in step 3 with (R)-3-amino-4-dimethylamino-butyric acid benzyl ester dihydrochloride to produce (R)-4-dimethylamino-3-(8-phenyl-octanoylamino)-butyric acid benzyl ester, which was hydrogenated in step 4.

Intermediate 32

(R)-4-Dimethylamino-3-(9-phenyl-nonanoylamino)-butyric acid

The title compound, m/e=361.5 ([M−H]⁻), was produced in analogy with intermediate 1, steps 3 and 4. Thus, commercially available 9-phenylnonanoic acid was coupled in step 3 with (R)-3-amino-4-dimethylamino-butyric acid benzyl ester dihydrochloride to produce (R)-4-dimethylamino-3-(9-phenyl-nonanoylamino)-butyric acid benzyl ester, which was hydrogenated in step 4.

Intermediate 33

(R)-4-Dimethylamino-3-(11-phenyl-undecanoylamino)-butyric acid

The title compound, m/e=391.5 ([M+H]⁺), was produced in analogy with intermediate 1, steps 3 and 4. Thus, commercially available 11-phenylundecanoic acid was coupled in step 3 with (R)-3-amino-4-dimethylamino-butyric acid benzyl ester dihydrochloride to produce (R)-4-dimethylamino-3-(11-phenyl-undecanoylamino)-butyric acid benzyl ester, which was hydrogenated in step 4.

Intermediate 34

(R)-4-Dimethylamino-3-(12-phenyl-dodecanoylamino)-butyric acid

The title compound, m/e=403.6 ([M−H]⁻), was produced in analogy with intermediate 1, steps 3 and 4. Thus, commercially available 12-phenyldodecanoic acid was coupled in step 3 with (R)-3-amino-4-dimethylamino-butyric acid benzyl ester dihydrochloride to produce (R)-4-dimethylamino-3-(12-phenyl-dodecanoylamino)-butyric acid benzyl ester, which was hydrogenated in step 4.

Example 1

(R)-3-[8-(3,4-Difluoro-benzyloxy)-octanoylamino]-4-trimethylammonio-butyrate

Potassium hydrogencarbonate (24 mg, 0.24 mmol) and iodomethane (106 mg, 0.74 mmol) were added to a solution of (R)-3-[8-(3,4-difluoro-benzyloxy)-octanoylamino]-4-dimethylamino-butyric acid (77 mg, 0.19 mmol) in methanol (2.5 mL). The reaction mixture was stirred at room temperature for 16 h, then diluted with chloroform (5 mL). Insoluble material was removed by filtration to afford (R)-3-[8-(3,4-difluoro-benzyloxy)-octanoylamino]-4-trimethylammonio-butyrate as a light yellow solid, m/e=429.3 ([M+H]⁺).

The following examples were prepared in analogy with example 1:

| Example | Compound name | Intermediate | m/e ([M + H]⁺) |
|---|---|---|---|
| 2 | (R)-3-[8-(2,5-Difluoro-benzyloxy)-octanoylamino]-4-trimethylammonio-butyrate | (R)-3-[8-(2,5-Difluoro-benzyloxy)-octanoylamino]-4-dimethylamino-butyric acid (intermediate 2) | 429.5 |
| 3 | (R)-3-[8-(2,4-Difluoro-benzyloxy)-octanoylamino]-4-trimethylammonio-butyrate | (R)-3-[8-(2,4-Difluoro-benzyloxy)-octanoylamino]-4-dimethylamino-butyric acid (intermediate 3) | 429.5 |
| 4 | (R)-3-[8-(2,3,4-Trifluoro-benzyloxy)-octanoylamino]-4-trimethylammonio-butyrate | (R)-4-Dimethylamino-3-[8-(2,3,4-trifluoro-benzyloxy)-octanoylamino]-butyric acid (intermediate 4) | 447.4 |

| Example | Compound name | Intermediate | m/e ([M + H]+) |
|---|---|---|---|
| 5 | (R)-3-[8-(Pentafluorophenyl-methoxy)-octanoylamino]-4-trimethylammonio-butyrate | (R)-4-Dimethylamino-3-(8-pentafluorophenylmethoxy-octanoylamino)-butyric acid (intermediate 5) | 483.3 |
| 6 | (R)-3-[8-(4-Trifluoromethyl-benzyloxy)-octanoylamino]-4-trimethylammonio-butyrate | (R)-4-Dimethylamino-3-[8-(4-trifluoromethyl-benzyloxy)-octanoylamino]-butyric acid (intermediate 6) | 461.4 |
| 7 | (R)-3-[8-(3-Fluoro-4-trifluoromethyl-benzyloxy)-octanoylamino]-4-trimethylammonio-butyrate | (R)-4-Dimethylamino-3-[8-(3-fluoro-4-trifluoromethyl-benzyloxy)-octanoylamino]-butyric acid (intermediate 7) | 479.4 |
| 8 | (R)-3-[8-(4-Methoxy-benzyloxy)-octanoylamino]-4-trimethylammonio-butyrate | (R)-4-Dimethylamino-3-[8-(4-methoxy-benzyloxy)-octanoylamino]-butyric acid (intermediate 8) | 423.3 |
| 9 | (R)-3-[8-(Biphenyl-4-ylmethoxy)-octanoylamino]-4-trimethylammonio-butyrate | (R)-3-[8-(Biphenyl-4-ylmethoxy)-octanoylamino]-4-dimethylamino-butyric acid (intermediate 9) | 469.3 |
| 10 | (R)-3-[8-(2-Fluoro-4-trifluoromethyl-benzyloxy)-octanoylamino]-4-trimethylammonio-butyrate | (R)-4-Dimethylamino-3-[8-(2-fluoro-4-trifluoromethyl-benzyloxy)-octanoylamino]-butyric acid (intermediate 10) | 479.2 |
| 11 | (R)-3-[8-(2,3,5,6-Tetrafluoro-4-methoxy-benzyloxy)-octanoylamino]-4-trimethylammonio-butyrate | (R)-4-Dimethylamino-3-[8-(2,3,5,6-tetrafluoro-4-methoxy-benzyloxy)-octanoylamino]-butyric acid (intermediate 11) | 495.4 |
| 12 | (R)-3-[8-(Naphthalen-1-ylmethoxy)-octanoylamino]-4-trimethylammonio-butyrate | (R)-4-Dimethylamino-3-[8-(naphthalen-1-ylmethoxy)-octanoylamino]-butyric acid (intermediate 12) | 443.5 |
| 13 | (R)-3-(8-Benzyloxy-octanoylamino)-4-trimethylammonio-butyrate | (R)-3-(8-Benzyloxy-octanoylamino)-4-dimethylamino-butyric acid (intermediate 13) | 393.3 |
| 14 | (R)-3-[8-(2-Fluoro-benzyloxy)-octanoylamino]-4-trimethylammonio-butyrate | (R)-4-Dimethylamino-3-[8-(2-fluoro-benzyloxy)-octanoylamino]-butyric acid (intermediate 14) | 411.4 |
| 15 | (R)-3-[8-(3-Fluoro-benzyloxy)-octanoylamino]-4-trimethylammonio-butyrate | (R)-4-Dimethylamino-3-[8-(3-fluoro-benzyloxy)-octanoylamino]-butyric acid (intermediate 15) | 411.5 |
| 16 | (R)-3-[8-(4-Fluoro-benzyloxy)-octanoylamino]-4-trimethylammonio-butyrate | (R)-4-Dimethylamino-3-[8-(4-fluoro-benzyloxy)-octanoylamino]-butyric acid (intermediate 16) | 411.5 |
| 17 | (R)-3-[8-(2,3-Difluoro-benzyloxy)-octanoylamino]-4-trimethylammonio-butyrate | (R)-3-[8-(2,3-Difluoro-benzyloxy)-octanoylamino]-4-dimethylamino-butyric acid (intermediate 17) | 429.3 |
| 18 | (R)-3-(10-Phenyl-decanoylamino)-4-trimethylammonio-butyrate | (R)-4-Dimethylamino-3-(10-phenyl-decanoylamino)-butyric acid (intermediate 18) | 391.2 |
| 19 | (S)-3-(10-Phenyl-decanoylamino)-4-trimethylammonio-butyrate | (S)-4-Dimethylamino-3-(10-phenyl-decanoylamino)-butyric acid (intermediate 19) | 391.4 |
| 20 | (R)-3-[10-(2-Fluoro-phenyl)-decanoylamino]-4-trimethylammonio-butyrate | (R)-4-Dimethylamino-3-[10-(2-fluoro-phenyl)-decanoylamino]-butyric acid (intermediate 20) | 409.4 |
| 21 | (R)-3-[10-(2,5-Dimethyl-phenyl)-decanoylamino]-4-trimethylammonio-butyrate | (R)-4-Dimethylamino-3-[10-(2,5-dimethyl-phenyl)-decanoylamino]-butyric acid (intermediate 21) | 419.5 |
| 22 | (R)-3-[10-(2,6-Dimethyl-phenyl)-decanoylamino]-4-trimethylammonio-butyrate | (R)-4-Dimethylamino-3-[10-(2,6-dimethyl-phenyl)-decanoylamino]-butyric acid (intermediate 22) | 419.4 |
| 23 | (R)-3-[10-(4-Methoxy-phenyl)-decanoylamino]-4-trimethylammonio-butyrate | (R)-4-Dimethylamino-3-[10-(4-methoxy-phenyl)-decanoylamino]-butyric acid (intermediate 23) | 421.1 |
| 24 | (R)-3-(10-Naphthalen-1-yl-decanoylamino)-4- | (R)-4-Dimethylamino-3-(10-naphthalen-1-yl- | 441.5 |

-continued

| Example | Compound name | Intermediate | m/e ([M + H]$^+$) |
|---|---|---|---|
| | trimethylammonio-butyrate | decanoylamino)-butyric acid (intermediate 24) | |
| 25 | (R)-4-Trimethylammonio-3-[10-(4-trifluoromethyl-phenyl)-decanoylamino]-butyrate | (R)-4-Dimethylamino-3-[10-(4-trifluoromethyl-phenyl)-decanoylamino]-butyric acid (intermediate 25) | 459.4 |
| 26 | (R)-3-[10-(3-Fluoro-phenyl)-decanoylamino]-4-trimethylammonio-butyrate | (R)-4-Dimethylamino-3-[10-(3-fluoro-phenyl)-decanoylamino]-butyric acid (intermediate 26) | 409.5 |
| 27 | (R)-3-[10-(2,3-Difluoro-phenyl)-decanoylamino]-4-trimethylammonio-butyrate | (R)-3-[10-(2,3-Difluoro-phenyl)-decanoylamino]-4-dimethylamino-butyric acid (intermediate 27) | 427.3 |
| 28 | (R)-3-(10-Thiophen-3-yl-decanoylamino)-4-trimethylammonio-butyrate | (R)-4-Dimethylamino-3-(10-thiophen-3-yl-decanoylamino)-butyric acid (intermediate 28) | 397.3 |
| 29 | (R)-3-(6-Phenyl-hexanoylamino)-4-trimethylammonio-butyrate | (R)-4-Dimethylamino-3-(6-phenyl-hexanoylamino)-butyric acid (intermediate 29) | 335.4 |
| 30 | (R)-3-(7-Phenyl-heptanoylamino)-4-trimethylammonio-butyrate | (R)-4-Dimethylamino-3-(7-phenyl-heptanoylamino)-butyric acid (intermediate 30) | 349.4 |
| 31 | (R)-3-(8-phenyl-octanoylamino)-4-trimethylammonio-butyrate | (R)-4-Dimethylamino-3-(8-phenyl-octanoylamino)-butyric acid (intermediate 31) | 363.4 |
| 32 | (R)-3-(9-Phenyl-nonanoylamino)-4-trimethylammonio-butyrate | (R)-4-Dimethylamino-3-(9-phenyl-nonanoylamino)-butyric acid (intermediate 32) | 377.4 |
| 33 | (R)-3-(11-Phenyl-undecanoylamino)-4-trimethylammonio-butyrate | (R)-4-Dimethylamino-3-(11-phenyl-undecanoylamino)-butyric acid (intermediate 33) | 405.5 |
| 34 | (R)-3-(12-Phenyl-dodecanoylamino)-4-trimethylammonio-butyrate | (R)-4-Dimethylamino-3-(12-phenyl-dodecanoylamino)-butyric acid (intermediate 34) | 419.4 |

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Polyvinylpyrrolidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene glycol 400 | 150.0 mg |
| Acetic acid | q.s. ad pH 5.0 |
| Water for injection solutions | ad 1.0 ml |

The active ingredient is dissolved in a mixture of polyethylene glycol 400 and water for injection (part). The pH is adjusted to 5.0 with acetic acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesiumstearate and the flavoring additives and filled into sachets.

The invention claimed is:

1. A compound of the formula

I wherein
$A^1$ is O or a bond,
m is selected from 3, 4, 5, 6, 7, 8, 9 and 10,
n is selected from 1, 2, 3, 4 and 5,
$R^1$ heteroaryl selected from the group consisting of pyridyl, thienyl and thiazolyl, said heteroaryl being unsubstituted or substituted by one, two or three groups selected from lower alkyl, halogen, lower halogenalkyl, lower alkoxy and phenyl, and pharmaceutically acceptable salts thereof.

2. The compound of formula I according to claim 1, wherein $A^1$ is O.

3. The compound of formula I according to claim 1, wherein $A^1$ is a bond.

4. The compound of formula I according to claim 1, wherein m is selected from 6, 7, 8, 9 and 10.

5. The compound of formula I according to claim 4, wherein m is 7.

6. The compound of formula I according to claim 1, wherein n is selected from the group consisting of 1, 2, 3 and 4.

7. The compound of formula I according to claim 6, wherein n is 1 or 2.

8. The compound of formula I according to claim 7, wherein n is 1.

9. The compound of formula I according to claim 1, wherein $R^1$ is thienyl.

10. A compound of formula I according to claim 1 having the formula

I-A

11. A compound of formula I according to claim 1, wherein said compound is (R)-3-(10-thiophen-3-yl-decanoylamino)-4-trimethylammonio-butyrate.

12. A process for the preparation of compounds of formula I as defined in claim 1, which process comprises reacting a tertiary amine of formula

II wherein $A^1$, m, n and $R^1$ are as defined hereinbefore, with a methylating agent in the presence of a base in a polar solvent to obtain a compound of formula

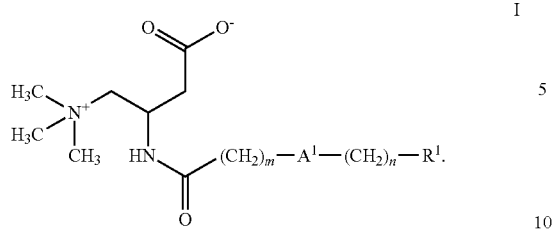

13. A pharmaceutical composition comprising a compound of formula I according to claim 1 and a pharmaceutically acceptable carrier and/or adjuvant.

14. A method for the treatment of diseases which are modulated by CPT2 inhibitors, comprising administering a compound of formula I according to claim 1 to a human being or animal.

15. A method for the therapeutic treatment of diseases which are modulated by CPT2 inhibitors, particularly for the therapeutic treatment of hyperglycemia, glucose tolerance disorders, diabetes and associated pathologies, non-insulin dependent diabetes mellitus, obesity, hypertension, insulin resistance syndrome, metabolic syndrome, hyperlipidemia, hypercholesterolemia, fatty liver disease, atherosclerosis, congestive heart failure and renal failure, which method comprises administering a compound of formula I according to claim 1 to a human being or animal.

16. A method for the therapeutic treatment of hyperglycemia and non-insulin dependent diabetes mellitus, comprising administering a compound of formula I according to claim 1 to a human being or animal.

* * * * *